United States Patent [19]

Ueda

[11] Patent Number: 4,463,928

[45] Date of Patent: Aug. 7, 1984

[54] CLAMP REGULATOR FOR TRANSFUSING LIQUID AND BLOOD

[76] Inventor: Shiro Ueda, 156, Fu Hsing North Rd., Taipei, Taiwan

[21] Appl. No.: 401,307

[22] Filed: Jul. 23, 1982

[51] Int. Cl.³ .............................................. F16L 55/14
[52] U.S. Cl. .................................................... 251/6
[58] Field of Search ............................................ 251/6

[56] References Cited

U.S. PATENT DOCUMENTS

4,285,492  8/1981  Bujan ...................................... 251/6
4,340,201  7/1982  Becker, Jr. .............................. 251/6
4,403,764  9/1983  Repplinger ............................. 251/6

Primary Examiner—Martin P. Schwadron
Assistant Examiner—Sheri Novack
Attorney, Agent, or Firm—Tak K. Sung

[57] ABSTRACT

The present invention relates to a clamp regulator for transfusing liquid and blood, and in particular to one which utilizes an adjustable wheel made integrally with an auxiliary wheel to compress a tubing on a conical surface so as to regulate the liquid flow passing through the tubing.

2 Claims, 13 Drawing Figures

CLAMP REGULATOR FOR TRANSFUSING LIQUID AND BLOOD

BACKGROUND OF THE INVENTION

Figure 7:
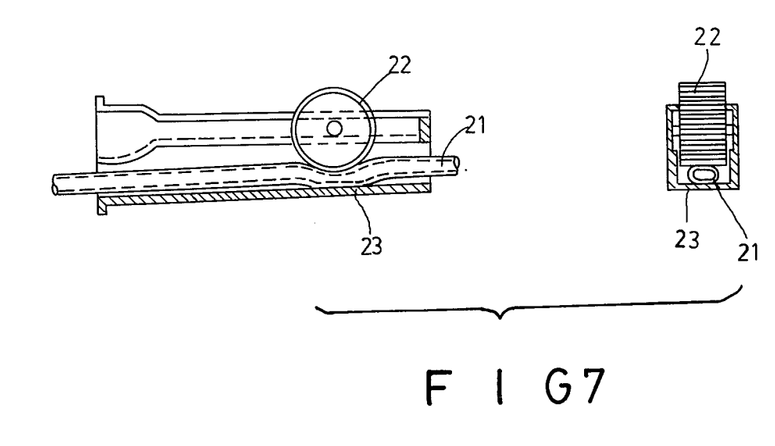
FIG. 7 is composed of two views of conventional roll regulator.
Figure 8:
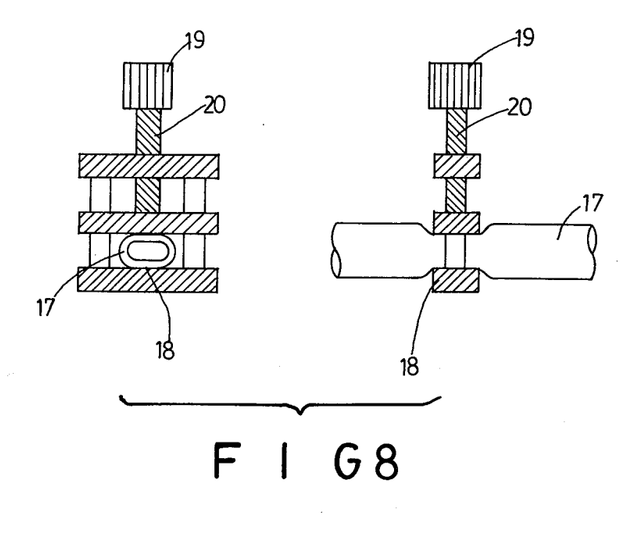
FIG. 8 is composed of two view of conventional screw regulator.

This new invention relates to a clamp regulator for transfusing liquid and blood. The clamps of prior regulators make use of a roller or screw. When a roller is used (FIG. 7), a tubing (21) is first inserted between the inclined surface (23) of the bottom and a round rod (22), and a the round rod (22) is translated by rotation so that the flow rate can be regulated by constricting the tubing (21). If the round rod excessively tends to be an ellipse or a plane, the flow rate cannot be changed easily; on the contrary, the flow rate is rapidly decreased and difficult to be slightly regulated. When a screw is used, a tubing (17) is placed under a plane and an adjustable rod (19) having screw thread (20) thereon can be rotated upward and downward to exert a compressive force on the plane so that the flow rate can be adjusted. This kind of device, in comparison with the roll, can be regulated more accurately. Usually, the flow rate is regulated to the required value when liquid or blood is transfused, then injection begins with one hand grasping a clamp and another hand a stop watch. Nevertheless, the inconvenience in rotating the adjustable rod (19) with a one hand and holding bottom (18) steady with another when using a screw clamp is a drawback.

Regardless of using a roller or screw clamp, there is a common drawback: during injection, the flow rate inside tubings (21), (17) will be gradually decreased with time. The gradual decrease of the force tending to recover the round shape of tubings (21), (17), the reaction force and the elastic force of material, will cause the tubings to sink at the central parts thereof, so that the area passed by the flow will diminish. Furthermore when the other liquid is injected during liquid transfusion or blood transfusion of mingled injection, tubings (21), (17) will oscillate on account of the adjusting portion being small and the clamps being mounted to the central parts of tubings (21), (17).

SUMMARY OF THE INVENTION

The present invention relates to a clamp regulator for transfusing liquid and blood which is especially designed to accurately and conveniently regulate the liquid flowing through the tubing.

The main purpose of the present invention is to offer a clamp regulator which can be simply adjusted for transfusing liquid and blood.

The second purpose of the present invention is to offer a clamp regulator for transfusing liquid and blood to adjust the flow rate inside the tubing; no mater how great a shock or blow is directed thereto or how long the time has elapsed, the initial flow rate inside the pipe tubing is maintained.

DETAILED DESCRIPTION OF THE PREFERRED EMBODIMENT:

With reference to the drawings and in particular FIGS. 1, 2, 3, 4 and 5, the clamp regulator according to the present invention comprises a clamp frame (1) having a first groove (2) for receiving an adjustable wheel (6) and a second groove (3) for receiving an auxiliary wheel (7). The two grooves are separated by a partition (4). The surfaces of the adjustable wheel (6) and the auxiliary wheel (7) are flat. With reference to FIG. 6, if the surface is circular, a clearance will be produced in the central part of the surface of the adjustable wheel; so flat surface is applied by reason of its being suitable for adjustment.

The method of adjusting the flow rate inside tubing (5) of clamp frame (1) makes use of the clearance between the inclined plane (9) of the bottom and the adjustable wheel (6) for effective flow rate adjustment. The characteristics of the present invention are that the width of second groove (2) equals the outside diameter of tubing (5), and the width of the adjustable wheel (6) is equal to the difference between the outside diameter of tubing (5) and four times the wall thickness of tubing (5). [Let the width of the adjustable wheel be A, outside diameter of tubing (5) be B, wall thickness of tubing (5) be C; therefore, the width of the adjustable wheel (6) is $A = B - 4C$]

Figure 5:
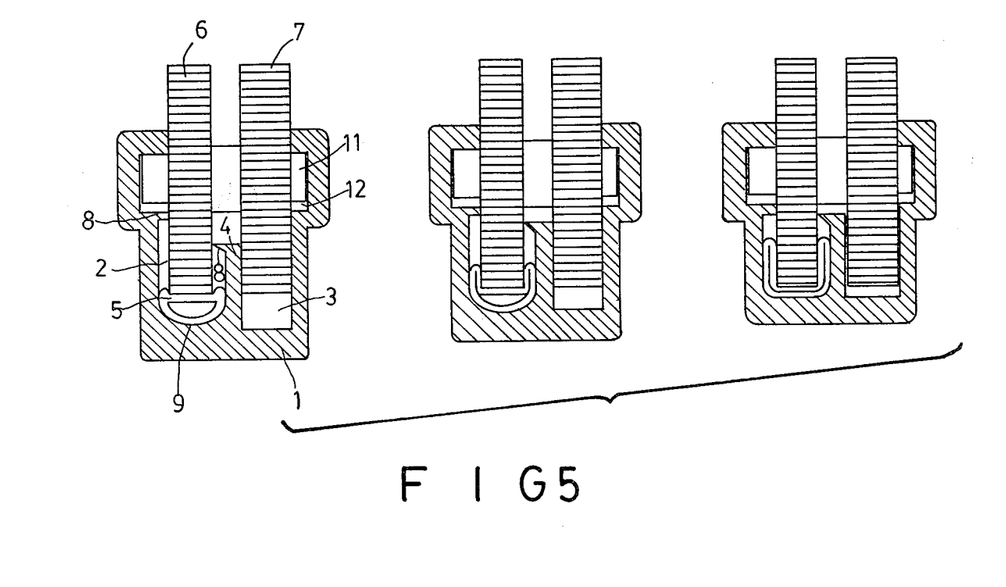
FIG. 5 is composed of three sectional views taken along lines III—III, IV—IV, V—V of FIG. 4 respectively.
Figure 6:
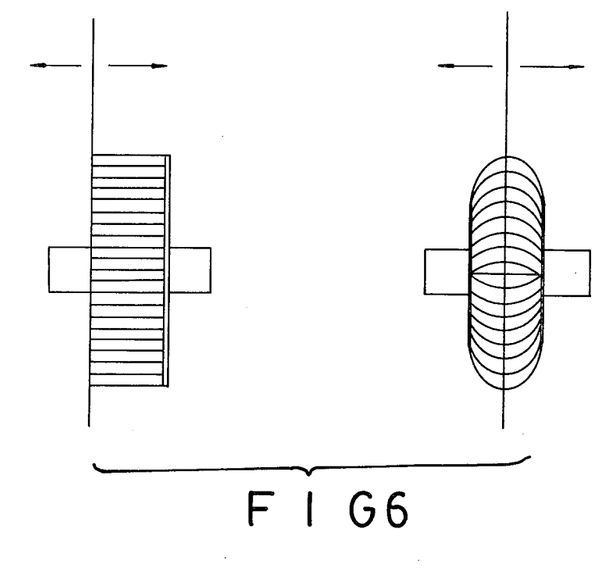
FIG. 6 is composed of two side views of different adjustable wheels.

With reference to FIG. 5, adjustable wheel (6) and auxiliary wheel (7) are integrally formed with an axle (11) which is slidably mounted in grooves (12), therefor, the first groove (2) being provided with a guided protuberance (8) for preventing undulation of the adjustable wheel (6), the second groove (3) is tightly engaged with the auxiliary wheel (7) and also has the function of preventing undulation of the adjustable wheel (6). Auxiliary wheel (7) serves to ensure that adjustable wheel (6) moves longitudinally along the center line of first groove (2) and guided protuberance (8) is designed to further ensure the alignment of the adjustable wheel with the center line of the first groove (2). A space clearance is provided between adjustable wheel (6) and first groove (2) of adjustable wheel (6) so that when tubing (5) is compressed, part of the tubing goes into this clearance.

The present invention can be exactly adjusted and can withstand blows or shock during transfusing liquid or blood; therefore, it can be used for accurate transfusion. Since wheels (6) and (7) have relatively large width, the present invention can be conveniently used for accurate transfusion.

Figure 1:
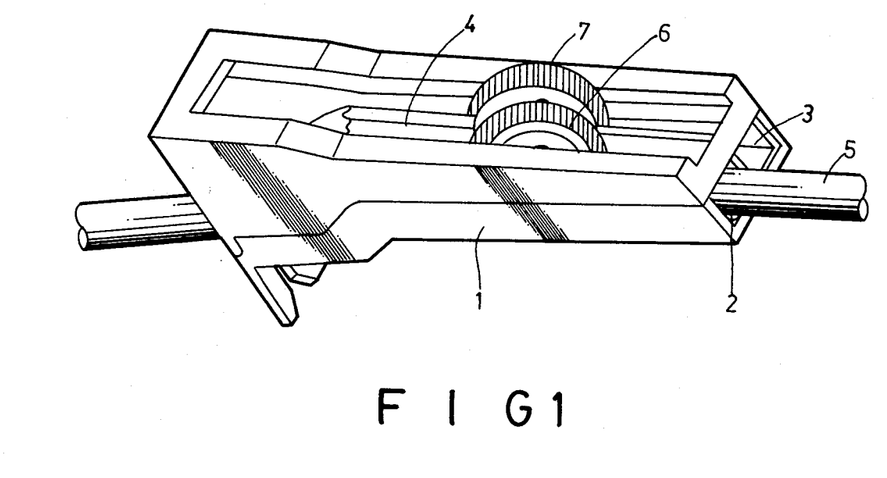
FIG. 1 is a perspective view of the present invention.
Figure 2:
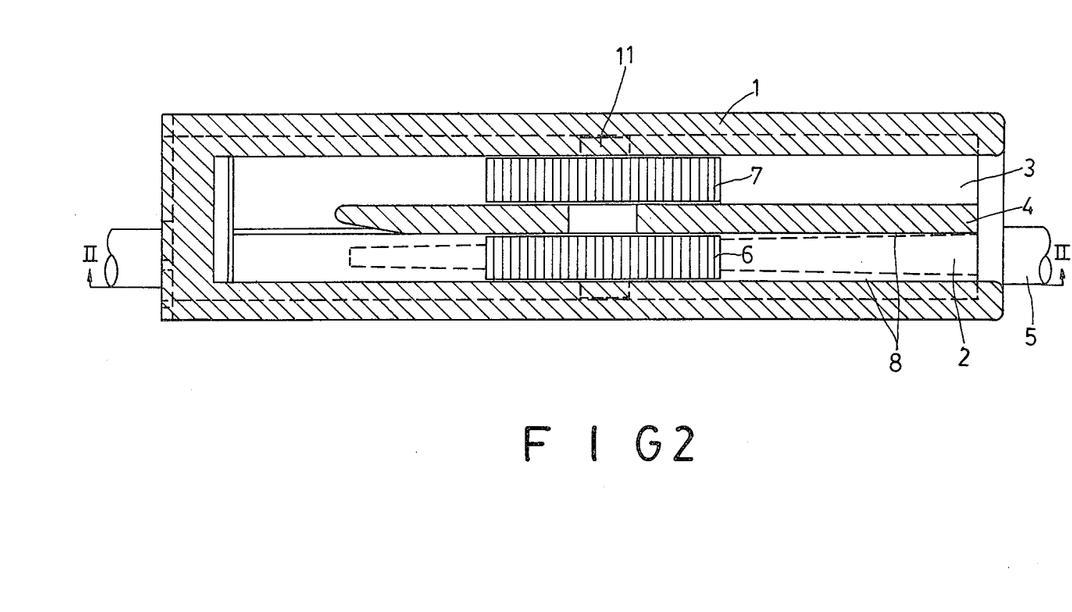
FIG. 2 is a full-sectional top view of the present invention.
Figure 3:
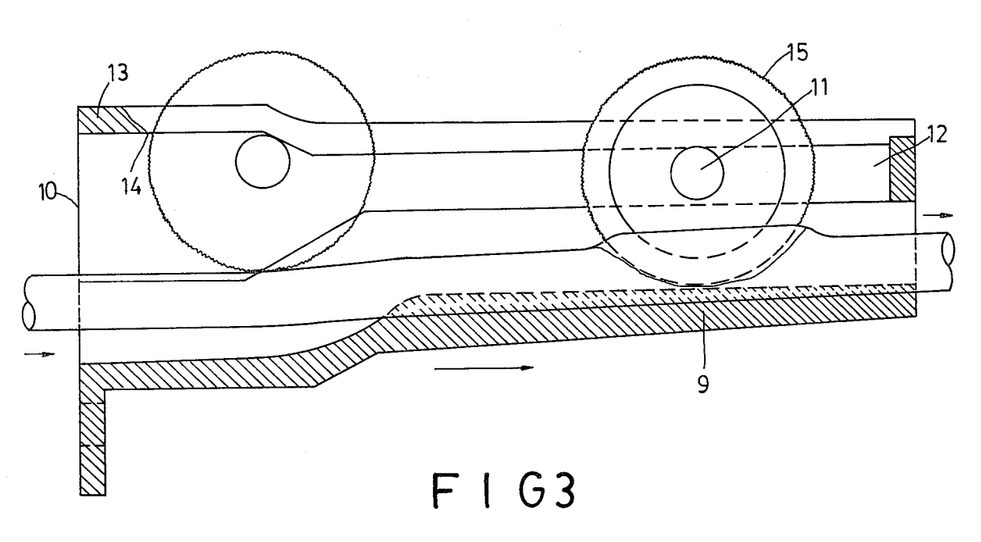
FIG. 3 is sectional view taken along line II—II of FIG. 2.
Figure 4:
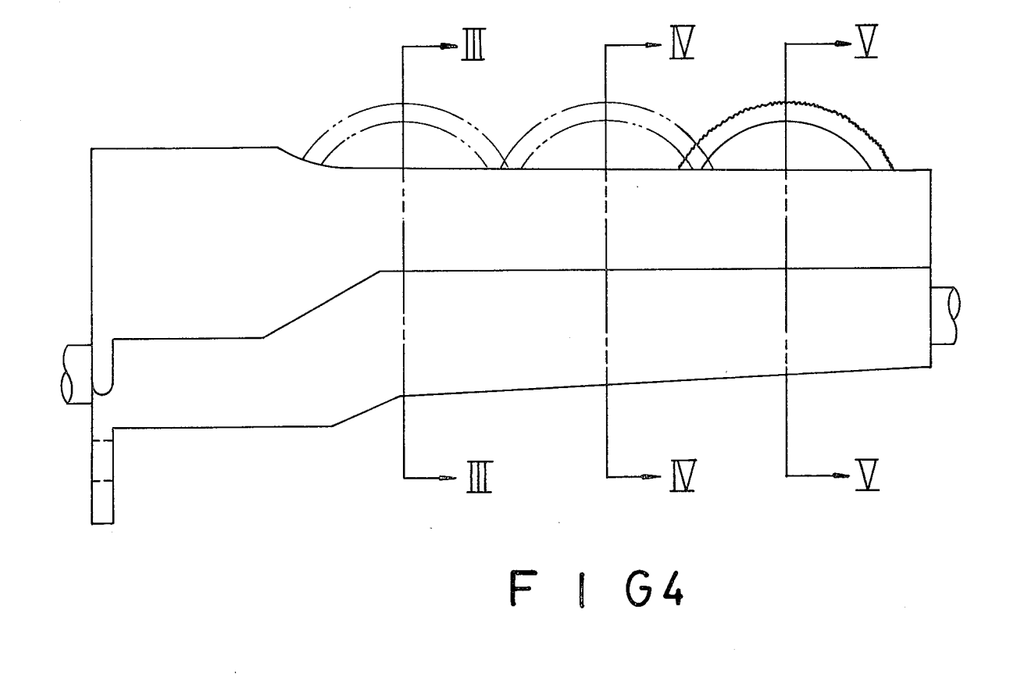
FIG. 4 is a view in which the adjustable wheel is in different positions.

FIG. 3 is the sectional view taken from line II—II of FIG. 2. The length of inlet (10) of the wheel and the outside diameter of adjustable wheel (6) are well-matched. Axle (11) is placed within the groove (12) of clamp frame (1). In the central space between adjustable wheel (6) and auxiliary wheel (7) is a partition (4) along which wheels (6) and (7) may be moved.

Tubing (5) is inserted into clamp frame (1). When the product is assembled or full flow rate is needed, it is necessary to move wheels (6) and (7) to return-preventing plate (13) thereby loosening tubing (5) from the adjusting position of clamp frame (1); therefore, full flow rate is attained. If the wheel is rotated too violently, the indentation (15) on the surface of the wheel will be scraped by knife edge (14) of return-preventing plate (13) and will engage with the return-preventing plate (13) thereby preventing wheels (6) and (7) from slipping. If wheels (6) and (7) are lifted a little bit, tubing (5) will be moved more easily. Furthermore, since the present invention utilizes two wheels (6) and (7) for regulation, a a nurse may apply a relatively small controlled force on both wheels (6) and (7) with her thumb to adjust wheels (6) and (7), thereby facilitating the operation of flow rate regulation.

In order to prevent changing, inclined surface (9) of the bottom is shaped into a conical surface; no matter how long the time has elapsed, the adjusting position is unchanged.

The change in the adjusted shape of tubing (5) and the change in the shape of the bottom of inclined surface (9) are shown in FIG. 5 which is composed of three sectional views in which the wheels are in different positions due to the rotary translation of the wheels while adjusting the flow rate.

When the space between adjustable wheel (6) and the bottom of inclined surface (9) is diminished, the shape of tubing (5) changes from round to elliptical due to pressure from adjustable wheel (6). In addition, the width of the adjustable wheel (6) is equal to the outside diameter of tubing (5) and tubing (5) is pressed, so that the rim of tubing (5) is forced into the clearance formed between adjustable wheel (6) and first groove (2). Accordingly, the inside cross-sectional area of tubing (5) is gradually decreased and the flow rate of the liquid therethrough is decreased.

In short, the liquid flow through tubing (5) can be slightly adjusted and decreased exactly by pressing wheels (6) and (7) so as to force the rim of the tubing (5) into the clearance formed between adjustable wheel (6) and first groove (2). No matter how great the shock or blow is, the flow rate can be adjusted accurately, and the wheel will not be loosened because the adjusting part is clamped in both sides. Also, by pressing with the wheels the sinking of the portion around the adjusting part of tubing (5).

From the description narrated above, the time can be measured and the regulator can be adjusted to obtain the required value, besides the flow rate initially adjusted will be unchanged with time; so it can be sure that the liquid or blood is being transfused steadily. The characteristics are completely shown during transfusing small amount of liquid.

I claim:

1. A clamp regulator for controlling liquid flow through a flexible tubing comprising:

a clamp frame having a first groove and a second groove, both extending longitudinally along the frame and having an inclined bottom to form deep and shallow ends, respectively, the first groove being provided with two guided protuberances and having a cross sectional area which increases from the deep to the shallow end;

an adjustable wheel slidably mounted into the clamp frame in such a way that the lower part of the wheel is positioned in the first groove, the adjustable wheel being adapted to engage the guided protuberances in the first groove to allow the wheel to move along the center line of the first groove; and an auxiliary wheel slidably mounted into the clamp frame in such a manner that the lower part of the wheel is located in the second groove, the auxiliary wheel being connected integrally to the adjustable wheel by an axle.

2. The regulator of claim 1 wherein the width A of the adjustable wheel, the outside diameter B of the tubing and the wall thickness C of the tubing satify the following equation $$A = B - 4C.$$

* * * * *